US011176617B1

(12) United States Patent  (10) Patent No.: US 11,176,617 B1
Kukreja  (45) Date of Patent: *Nov. 16, 2021

(54) MOBILE SUBMISSION OF PHARMACY INSURANCE INFORMATION

(71) Applicant: CVS Pharmacy, Inc., Woonsocket, RI (US)

(72) Inventor: Vijay I. Kukreja, Cumberland, RI (US)

(73) Assignee: CVS Pharmacy, Inc., Woonsocket, RI (US)

( * ) Notice: Subject to any disclaimer, the term of this patent is extended or adjusted under 35 U.S.C. 154(b) by 385 days.

This patent is subject to a terminal disclaimer.

(21) Appl. No.: 16/389,537

(22) Filed: Apr. 19, 2019

Related U.S. Application Data

(63) Continuation of application No. 14/944,535, filed on Nov. 18, 2015, now Pat. No. 10,319,038.

(51) Int. Cl.
| | | |
|---|---|---|
| *G06Q 40/08* | (2012.01) | |
| *G06K 19/06* | (2006.01) | |
| *G06K 19/04* | (2006.01) | |
| *G06Q 50/22* | (2018.01) | |

(52) U.S. Cl.
CPC ........... *G06Q 40/08* (2013.01); *G06K 19/042* (2013.01); *G06K 19/06009* (2013.01); *G06Q 50/22* (2013.01)

(58) Field of Classification Search
CPC .. G06Q 40/08; G06Q 50/22; G06K 19/06009; G06K 19/042
See application file for complete search history.

(56) References Cited

U.S. PATENT DOCUMENTS

| | | | | |
|---|---|---|---|---|
| 8,694,332 B2* | 4/2014 | Martin | ............... | G16H 20/10 705/2 |
| 8,733,641 B1* | 5/2014 | Drew | ............... | G16H 40/20 235/381 |
| 2001/0047281 A1* | 11/2001 | Keresman, III | ...... | G16H 40/67 705/2 |
| 2006/0117021 A1* | 6/2006 | Sidney | ............... | G16H 10/60 |
| 2006/0151599 A1* | 7/2006 | Awatsu | ............... | G07C 9/257 235/380 |
| 2009/0173784 A1* | 7/2009 | Yang | ............... | G06Q 20/40 235/380 |
| 2011/0166884 A1* | 7/2011 | Lesselroth | ........... | G06Q 10/06 705/3 |

(Continued)

FOREIGN PATENT DOCUMENTS

| | | | | |
|---|---|---|---|---|
| WO | 2008/092043 | | 7/2008 | |
| WO | WO-2008092043 A2 * | 7/2008 | ............. | G06Q 10/10 |

OTHER PUBLICATIONS

CVS/Caremark:Your Benefits.Delivered With Care, Oct. 30, 2015, WebArchives, p. 1 (Year: 2015).*

(Continued)

*Primary Examiner* — Bijendra K Shrestha
(74) *Attorney, Agent, or Firm* — Patent Law Works LLP

(57) ABSTRACT

If a user of a client device is authenticated with a pharmacy service, the user is prompted to capture an image of an insurance card; if the user is not authenticated, the user is further prompted to input patient information. Information is extracted from the insurance card and it and the patient information are transmitted to a pharmacy for processing.

20 Claims, 8 Drawing Sheets

(56) References Cited

U.S. PATENT DOCUMENTS

| | | | | |
|---|---|---|---|---|
| 2011/0185178 A1* | 7/2011 | Gotthardt | ............. | H04L 9/3234 |
| | | | | 713/172 |
| 2011/0307265 A1* | 12/2011 | Bannis | ................... | G06Q 10/10 |
| | | | | 705/2 |
| 2012/0292388 A1* | 11/2012 | Hernandez | ......... | G06Q 20/3276 |
| | | | | 235/379 |
| 2013/0096938 A1* | 4/2013 | Stueckemann | ......... | G06F 19/00 |
| | | | | 705/2 |
| 2014/0229194 A1* | 8/2014 | Brooks | ................. | G06Q 40/08 |
| | | | | 705/2 |
| 2015/0106897 A1* | 4/2015 | Davis | ..................... | G06F 21/32 |
| | | | | 726/7 |
| 2017/0032101 A1* | 2/2017 | Skoda | .................... | G16H 40/20 |
| 2017/0041784 A1* | 2/2017 | Watanabe | ............... | H04L 63/08 |
| 2017/0161458 A1* | 6/2017 | Rourke | ................. | G16H 20/10 |

OTHER PUBLICATIONS

Fiserv: Banking in a Snap: Mobile Image Capture Can Transform Financial Service, 2015, pp. 1-8 (Year: 2015).*

Pofeldt, Elaine: Card Updater Services Keep Customer's Auto-Payments Flowing, Nov. 30, 2015, pp. 1-10 (Year: 2015).*

CVS/Caremark, "CVS/caremark: Your Benefits Delivered with Care," Oct. 30, 2015, retrieved from https://web.archive.org/web/20151030040514/https://www.caremark.com/wps/portal in Jan. 13, 2019, 1 pg.

Pofeldt, "Card Updater Services Keep Customers' Auto-Payments Flowing," Nov. 30, 2015, retrieved from https://www.creditcards.com/credit-card-news/card-updater-services-auto-pay-1585.php on Jan. 12, 2019, pp. 1-10.

Senior Corps, "How Do I Change My Information with Medicare?" Oct. 22, 2015, retrieved from https://web.archive.org/web/20151022080305/http://www.seniorcorps.org/medicare/how-do-i-change-my-information . . . on Jan. 13, 2019, pp. 1-3.

* cited by examiner

MOBILE SUBMISSION OF PHARMACY INSURANCE INFORMATION

CROSS REFERENCE TO RELATED APPLICATIONS

The present application is a continuation of U.S. patent application Ser. No. 14/944,535, filed Nov. 18, 2015, and entitled "Mobile Submission of Pharmacy Insurance Information," the entirety of which is hereby incorporated by reference.

TECHNICAL FIELD

Embodiments of the present invention relate generally to pharmaceutical sales and, more particularly, to updating and/or renewing patient insurance information.

BACKGROUND

Accurate insurance information is necessary for payment and claims processing for pharmacy services. If a patient does not have accurate and up-to-date insurance information on file with the pharmacy, prescription fills may be delayed, leading to additional wait times, drugs returned to stock, and additional effort from pharmacy staff to address the issue (such as, for example, phone calls, checking eligibility, etc.).

In existing methods, when a person receives a new or updated insurance card, he or she must give the pharmacy the new or updated card information for data entry in order to use that insurance. The primary method for providing this information to the pharmacy is to physically present the card to staff and wait while the data is entered. One problem with this method is the inconvenience from increased wait times and/or additional trips to the store.

In some other existing methods, patients read the insurance information to pharmacy staff over a telephone. One problem with this method is that there are thousands of differing card layouts, and without being able to see the card, it is difficult for the pharmacy staff to identify which fields are needed from the card. Often, patients are not familiar with insurance card data will not know which fields to give the staff, resulting in difficulties and inaccuracies when exchanging the information. A need therefore exists for a more convenient and versatile system and method for entering new or updating existing insurance information.

SUMMARY

Embodiments of the present invention include systems and methods for facilitating the entry and/or updating of patient insurance information. In various embodiments, a user who is authenticated with a pharmacy service is prompted to capture images of his or her new or updated insurance card; the images and/or information extracted therefrom are transmitted to a pharmacy for processing. If the user is not authenticated (and/or does not even have a user account), the user is further prompted to enter patient information (e.g., name, date of birth, etc.), which is then transmitted to the pharmacy with the images.

In one aspect, a system for entering new or updating existing patient insurance information includes a non-volatile computer memory for storing an image of a new or updated insurance card; a network interface configured for receiving new or updated insurance information from a user of a client device over a computer network; and a computer processor configured for executing software instructions to: detect whether the user is authenticated with a pharmacy service, wherein the pharmacy service comprises patent information; if the user is authenticated with the pharmacy service, cause a first graphical-user interface to be displayed to the user on the screen of the client device, the first graphical-user interface comprising a prompt to capture an image of the insurance card; if the user is not authenticated with the pharmacy service, cause a second graphical-user interface to be displayed to the user on the screen of the client device, the second graphical-user interface comprising (i) the prompt to capture the image of the insurance card and (ii) a data-entry prompt for capturing patient information; extract information from the image of the insurance card; and electronically transmit the patient information and the extracted information from the image of the insurance card to a pharmacy for processing.

Upon successful transmission of the patent information and the extracted information, a confirmation of success may be caused to be displayed on the screen of the client device. The instructions to extract information from the image of the insurance card may include optical-character recognition, cropping, or scanning a barcode. The new or updated insurance card is may be associated with a person other than the user and wherein the patient information comprises information about the person other than the user. The person other than the user may include a family member of the user or other person associated with the insurance card. The pharmacy service may further include (i) patient information for the person other than the user and (ii) data defining a relationship between the user and the person other than the user. The pharmacy service may further include data comprising an authorization from the person other than the user allowing the user permission to submit the image of the insurance card on behalf of the person other than the user. The pharmacy may be selected based on a default pharmacy of the user, a last-used pharmacy of the user, or user input. A message may be transmitted to the client device of the user comprising an indication that an update to the insurance card is needed.

In another aspect, a method for entering new or updating existing patient insurance information includes detecting whether a user of a client device is authenticated with a pharmacy service, wherein the pharmacy service comprises patent information; if the user is authenticated with the pharmacy service, causing a first graphical-user interface to be displayed to the user on the screen of the client device, the first graphical-user interface comprising a prompt to capture an image of an insurance card; if the user is not authenticated with the pharmacy service, causing a second graphical-user interface to be displayed to the user on the screen of the client device, the second graphical-user interface comprising (i) the prompt to capture the image of the insurance card and (ii) a data-entry prompt for capturing patient information; extracting information from the image of the insurance card; and electronically transmitting the patient information and the extracted information from the image of the insurance card to a pharmacy for processing.

Upon successful transmission of the patent information and the extracted information, a confirmation of success may be caused to be displayed on the screen of the client device. The instructions to extract information from the image of the insurance card may include optical-character recognition, cropping, or scanning a barcode. The new or updated insurance card is may be associated with a person other than the user and wherein the patient information comprises information about the person other than the user. The person other than the user may include a family member of the user or other person associated with the insurance card. The pharmacy service may further include (i) patient information for the person other than the user and (ii) data defining a relationship between the user and the person other than the user. The pharmacy service may further include data comprising an authorization from the person other than the user allowing the user permission to submit the image of the insurance card on behalf of the person other than the user. The pharmacy may be selected based on a default pharmacy of the user, a last-used pharmacy of the user, or user input. A message may be transmitted to the client device of the user comprising an indication that an update to the insurance card is needed.

These and other objects, along with advantages and features of the present invention herein disclosed, will become more apparent through reference to the following description, the accompanying drawings, and the claims. Furthermore, it is to be understood that the features of the various embodiments described herein are not mutually exclusive and can exist in various combinations and permutations.

BRIEF DESCRIPTION OF THE DRAWINGS

In the drawings, like reference characters generally refer to the same parts throughout the different views. In the following description, various embodiments of the present invention are described with reference to the following drawings, in which.

DETAILED DESCRIPTION

Figure 1:
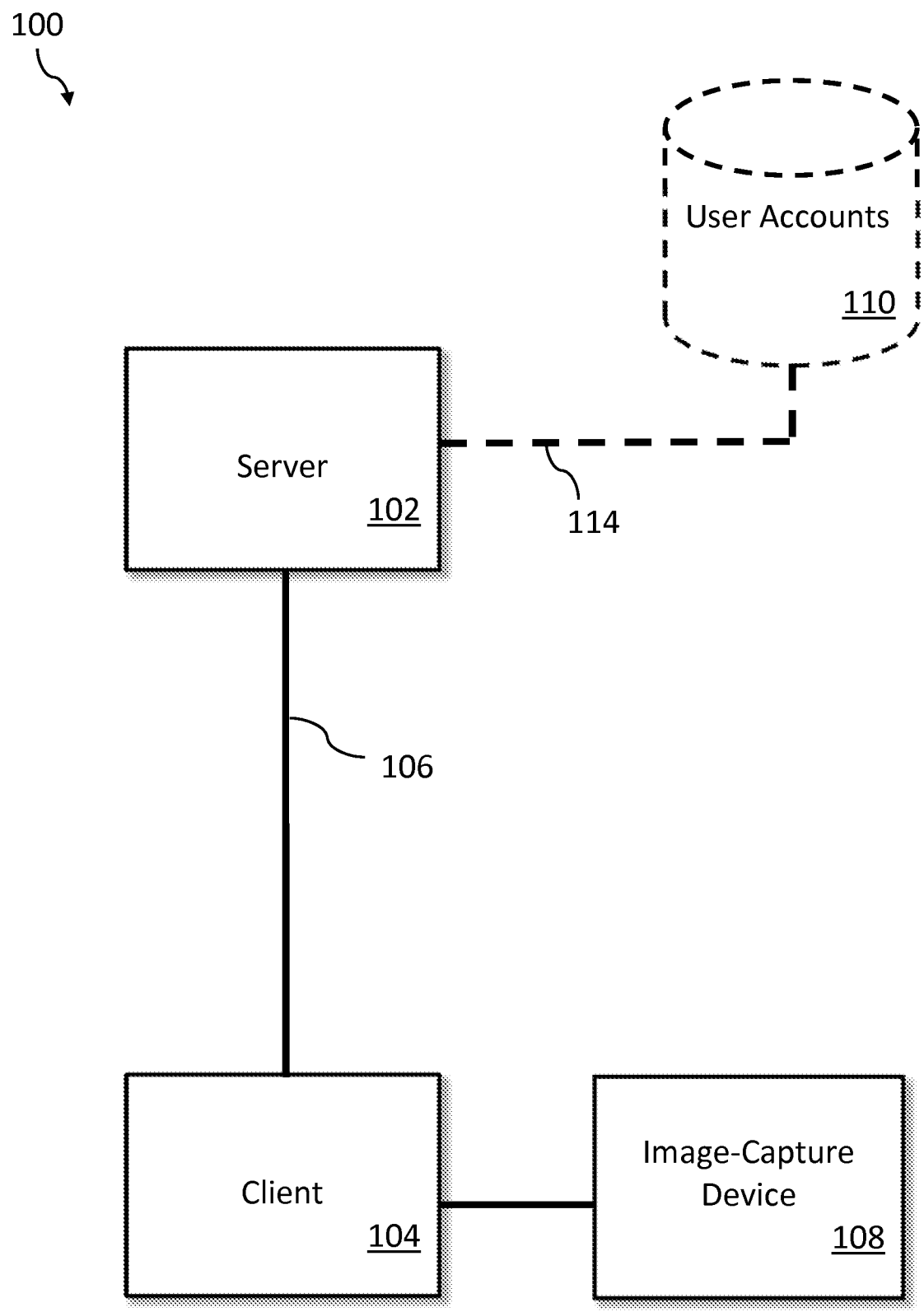
FIG. 1 illustrates a computing environment in accordance with an embodiment of the present invention.

Various embodiments of the present invention include systems and methods for allowing patients to submit captured images (and/or data extracted from those images) of their new or updated insurance cards electronically, thereby allowing the patients to provide this information from any convenient location and providing the pharmacy staff clear, legible information. In various embodiments, with reference to FIG. 1, a computing environment 100 includes a computer server 102 or similar system that is configured to receive, from a remote client device 104, an electronic image of an insurance card (and/or or information extracted therefrom) via a network 106 (such as the Internet or other network). In various embodiments, the client 104 is an electronic device such as a smartphone, tablet, or computer and includes or is connected to an image-capture device 108, such as a camera, integrated camera, scanner, or similar device. The server 102 and/or client 104, in some embodi-ments, extracts information from the image related to insurance information. In some embodiments, the user of the client 104 is authenticated with a pharmacy service (which may be wholly or partially hosted on the server 102); the server 102 may communicate with a user-account database 110 via a network link 114 that includes information about the user, such as his or her name, address, phone number, date of birth, and gender. In other embodiments, the user of the client 104 is not authenticated with the pharmacy service; in these embodiments, the client 104 prompts the user for this patient information. Once the patient information is accessed and/or transmitted to the server 102 and/or client 104, it is transmitted to a pharmacy for processing. These aspects of the invention are described in greater detail below; one of skill in the art will understand, however, that the invention is not limited to only the configuration of the environment 100 and that other configurations of the server 102 and client device 104 are within the scope of the present invention. For example, any number of servers 102 and clients 104 may be used; in some embodiments, some or all of the functionality of the server 102 may be implemented on the client 104.

Figure 2:
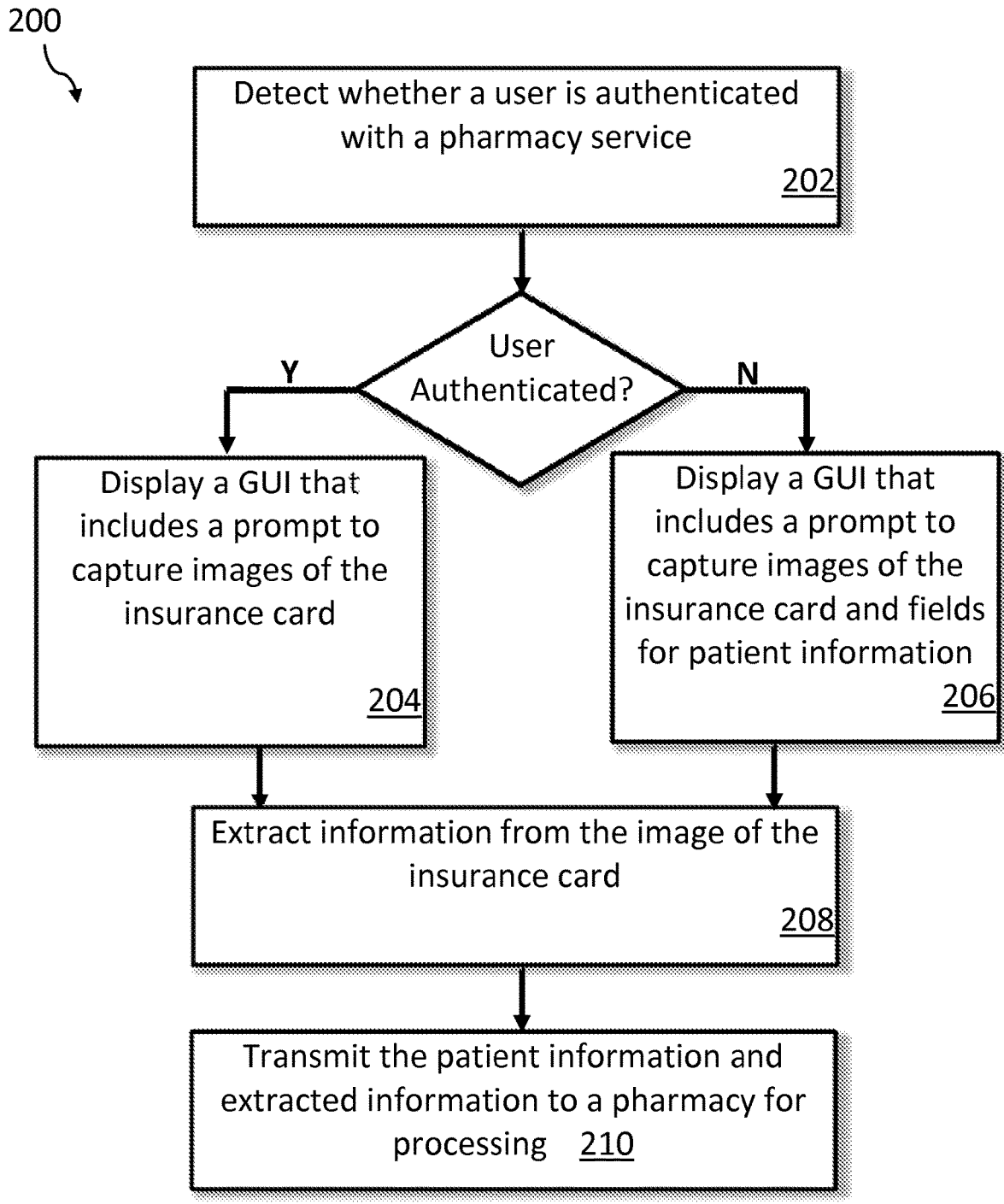
FIG. 2 illustrates a method for updating insurance information in accordance with an embodiment of the present invention.

FIG. 2 illustrates one embodiment of a method 200 for electronic processing of a new or updated insurance card. In a first step, the server 102 and/or client 104 detects (202) whether a user is authenticated with a pharmacy service running wholly or partially on the server 102 and/or client 104. In some embodiments, the user has an existing account on the server 102 that includes, for example, information regarding his or her name, address, phone number, gender, date of birth, billing information (e.g., credit-card information), preferred pharmacy, last-used pharmacy, or any other similar information; this information may be stored in the user-account database 110. The user may authenticate him or herself to the server 102 via, for example, entering a username and password into the client 104, by scanning biometric data (e.g., fingerprint or heartbeat), with the client 104 or by any other method of authentication known in the art. The authentication information may be transmitted to the server 104 for comparison against verified authentication information and/or processed at the client 104.

In some embodiments, the client 104 determines whether the user is authenticated with the pharmacy service. If, for example, the user has previously authenticated him or herself with the pharmacy service using the client 104, the client 104 may store a file, variable, token, or similar construct in volatile or non-volatile computer memory that indicates successful authentication. The client 104 may examine the file or token and, depending on the state thereof, infer that the user is authenticated. The file or token may be reset if, for example, a certain amount of time elapses, the user logs out of the client 104, the user makes an unsuccessful login attempt, or any similar reason.

In other embodiments, the client 104 queries the server 102 to determine whether the user is authenticated with the pharmacy service. The server 104 may similarly store a file, variable, token, or similar construct in volatile or non-volatile computer memory that indicates successful authentication. The server 102 may identify the user based on a username, email address, device MAC address, client 104 IP address, or any other similar information, and check to see if the user owns a user account in the user-account database 110.

If the user is authenticated, the server 102 and/or client 104 causes the client 104 to display (204) a graphical-user interface that includes a prompt to capture one or more images of the user's insurance card. The user may be prompted to capture one image of the front of the card, two images of the front and back of the card, or any other number of images. The interface may access the image-capture device 108 (via, for example, an application-programming interface) and allow the user to preview and capture one or more images of the card. For example, a window on the interface may display a preview image of the card and, if the user is satisfied, the user captures the images by activating a control on the interface, such as a button. In some embodiments, the interface automatically scans the card for a pattern of encoded data, such as a bar code, and detects and extracts information therefrom without requiring interaction from the user.

If the user is not authenticated, the server 102 and/or client 104 may prompt the user for authentication and/or account-creation information. In other embodiments, however, the server 102 and/or client 104 permit the user to proceed with the process of updating his or her insurance card without authenticating and/or creating a user account with the server 102. In some embodiments, the server 102 and/or client 104 cause the client 104 to display (206) a graphical user interface that includes the prompt to capture one or more images of the user's insurance card as well as a data-entry prompt to capture information about the user. The data-entry prompt may include one or more text-entry boxes with which the user may enter patient information, such as his or her name, phone number, address, date of birth, gender, or similar information. The user may enter the information using a keyboard, touchscreen, mouse, voice input, or any similar method.

Instead of or in addition to the information entered by the user, the client 104 may additionally prompt the user to capture an image of an identification card belonging to the user, such as a driver's license, using the image-capture device 108. The server 102 and/or client 104 may then extract the patient information from the image of the identification card.

In some embodiments, the server 102 and/or client 104 extract (208) information from the image of the insurance card. For example, one or more optical-character recognition algorithms may be run on the image (by the server 102 and/or client 104) to recognize and capture any text present originally on the card and represented in the image. This text may include, for example, an insurance provider name, a patient name, an account number, or any other similar information. Non-character-based information, such as a card color or shape or an insurance-provider logo, may similarly be extracted.

In some embodiments, the image of the insurance card includes information encoded into a design, such as a one-dimensional or two-dimensional bar code. The server 102 and/or client 104 may analyze the image to detect the presence of the bar code and extract the characters, numbers, or other information encoded therein. In other embodiments, the client 104 includes bar-code scanning software and/or hardware that detects the presence of the bar code in the captured image and automatically extracts information encoded therein; in these embodiments, the client 104 may transmit to the server 102 only the information extracted from the bar code and not the entire image.

Once information has been extracted from the image of the insurance card, the patient information (whether sourced from the user account or entered by the user) and extracted information is transmitted (210) to a facility, such as a pharmacy, for processing. In other embodiments, no information is extracted from the image; the server 102 and/or client 104 transmits the image to the facility without performing any processing of the image.

There may be a plurality of pharmacies capable of receiving the transmitted data and processing the insurance-card entry/update for the user. In one embodiment, the user specifies a preferred pharmacy in his or her user account, and the user's information is transmitted thereto via the Internet, other data network, telephone network, or any other type of network. In another embodiment, the user-account database 110 includes a location of a pharmacy last visited by the user or a location of a pharmacy most frequently visited by the user, and the user's information is transmitted thereto. The client 104 may display a confirmation dialog to the user to confirm the location of the selected pharmacy. If the user is not authenticated to a pharmacy service, the client 104 may prompt the user to enter a pharmacy location, select a pharmacy from a list or menu of available/proximate pharmacies, or select a pharmacy any other way.

In various embodiments, the insurance card may be associated with a person other than the user instead of or in addition to being associated with the user. In some embodiments, the other person is a family member of the user; in other embodiments, the other person is unrelated to the user. The server 102 and/or client 104 may require that the user be authenticated before permitting the user to update the insurance information of the other person. In some embodiments, if the other person is unrelated to the user, the server 102 and/or the client 104 requires that the other person has provided some indication that he or she permits the user to update the insurance information, such as an electronic signature.

The insurance card (and associated health insurance) may be provided by an employer of one spouse, for example, and the insurance benefits may extend to the other spouse, children, parents, or other people related to the spouse. The user may therefore use the client 104 to not only add or update insurance information for him or herself but also add or update insurance information for a family member. In various embodiments, patient information for the family members (such as date of birth) is associated with the user account of the user; the user had previously or concurrently provided this information to the server 102. In other embodiments, the family members have their own user accounts on the server 102, and the user's account includes pointers or other links to the user accounts of the family members. In other embodiments, the family members do not have user accounts on the server 102; the client 104 may therefore prompt the user to enter the names, addresses, phone numbers, etc. for the family members.

In some embodiments, the insurance card is associated only with one or more other persons and not with the user. For example, each spouse may have their own, separate health insurance provided by their employers (and corresponding separate insurance cards), and the user may update the insurance information of both spouses using the client 104. When the user updates his or her own insurance information, the client 104 processes the information as described above. When the user updates the spouse's insurance information (using the spouse's card), the user captures an image of the spouse's card and enters the spouse's patient information using the client 104.

Figure 3:
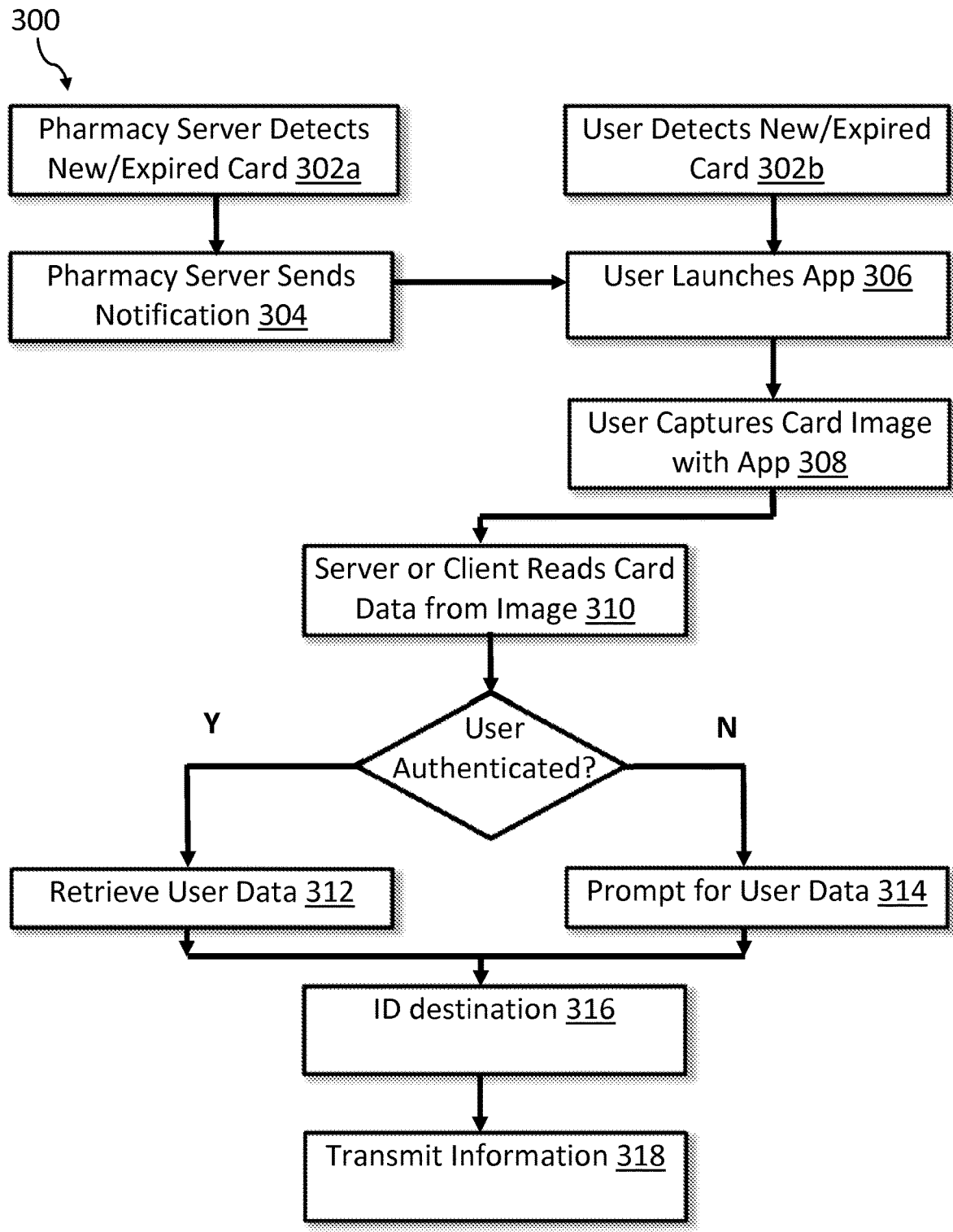
FIG. 3 illustrates a method for updating insurance information in accordance with an embodiment of the present invention.

FIG. 3 illustrates a method 300 in accordance with embodiments of the present invention. A user may be associated with a new or expired insurance card representing a new or expired account with a health, dental, or similar insurance provider. A pharmacy server may detect (302a) the new or expired card when the user attempts to use it or when a known expiration date of the card arrives; the pharmacy server may as a result send (304) a notification to the user so informing him or her. Alternatively or in addition, the user may detect (302*b*) the new or expired card.

In response to the detection by the user and/or pharmacy, the user launches (306) a software application on his or her computing device, such as a smartphone, tablet, or other computer. In one embodiment, the application launches automatically in response to the detection. As discussed above, the application may prompt the user to capture (308) one or more electronic images of the card (which may include encoding the picture in one of any image formats, such as BMP, JPEG, or TIFF and/or capturing bar-code information from the image). The server 102 and/or the client 104 may read (310) insurance-card data from the image using, for example, optical-character recognition, bar-code scanning, or any other similar method or technique.

The server 102 and/or the client 104 may determine if the user is authenticated with a pharmacy service; if so, the user's data is retrieved (312) therefrom. If not, the user is prompted (314) for user data (such as his or her name, address, phone number, etc.). As discussed above, a destination pharmacy is identified (316) and the information is transmitted (318) thereto.

Figure 4:
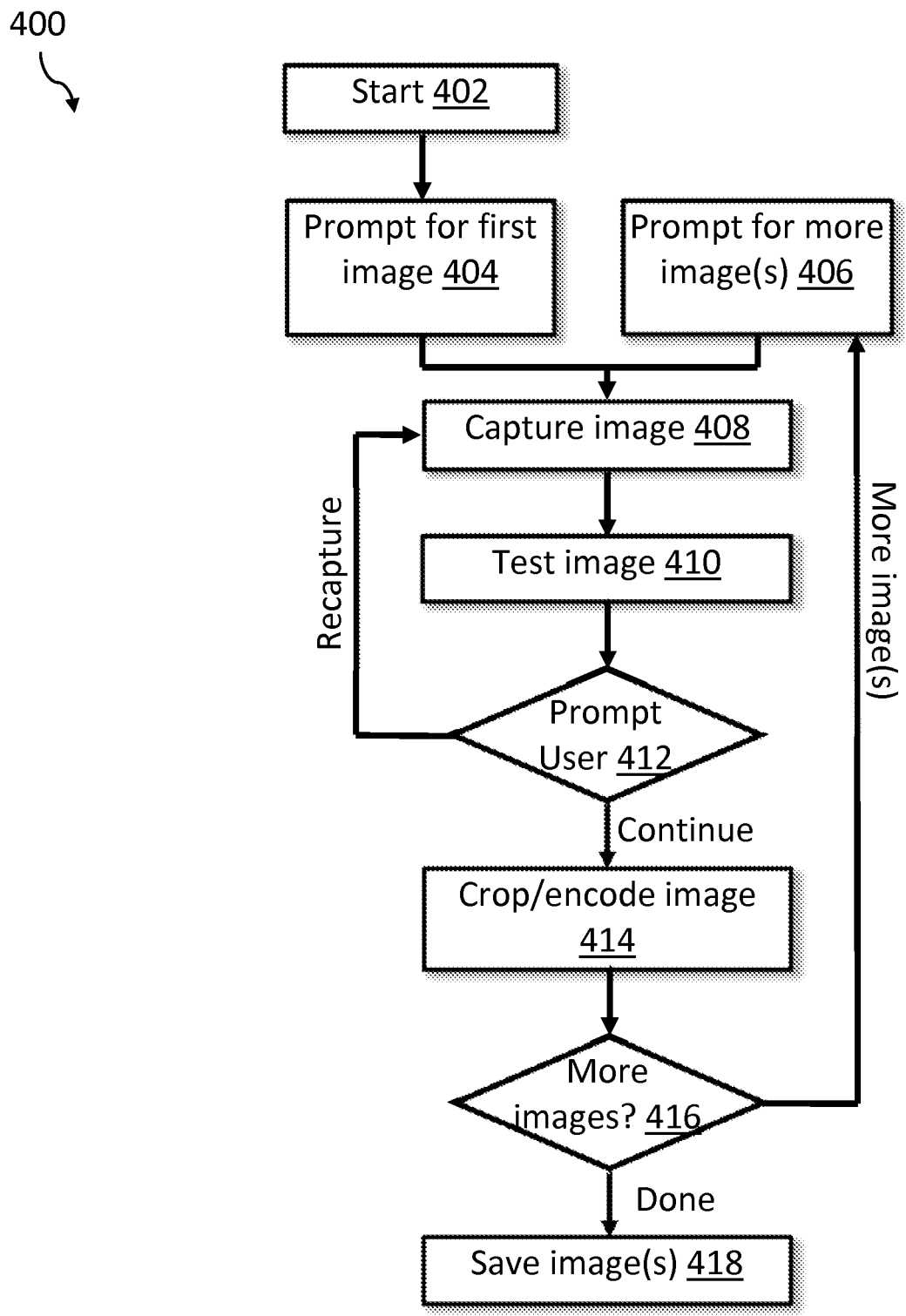
FIG. 4 illustrates a method for capturing images in accordance with an embodiment of the present invention.

FIG. 4 illustrates a method 400 for capturing one or more images of an insurance card. The method begins (402) with the prompting (404) of the user to capture a first image by, for example, displaying a graphical-user interface on the screen of the client 104. The user captures (408) the image using the client device 104 and the image-capture device 108. The image is then tested (410) by the client 104 and/or user for quality; for example, the client 104 may reject the image if too much blurriness or too little light is detected. The user may similarly deem the image insufficient. If so, the image is recaptured (408).

Once an image of sufficient quality is captured, the image is cropped, encoded, or otherwise processed (414). The image may be cropped to a specific aspect ratio and/or encoded to Base64 format. If more images are required (416) (of, for example, a back side of the card), the user is prompted to enter (406) more images. The prompt may include a notice to the user to flip over the card to capture the back side. In some embodiments, an image of the back side of the card is required only if sufficient information cannot be determined from the image of the front of the card. Once all required images are captured, the images are saved (418). In some embodiments, JSON is used to upload the Base64 format images to the server 102, and a progress indicator is shown to the user.

Figure 5:
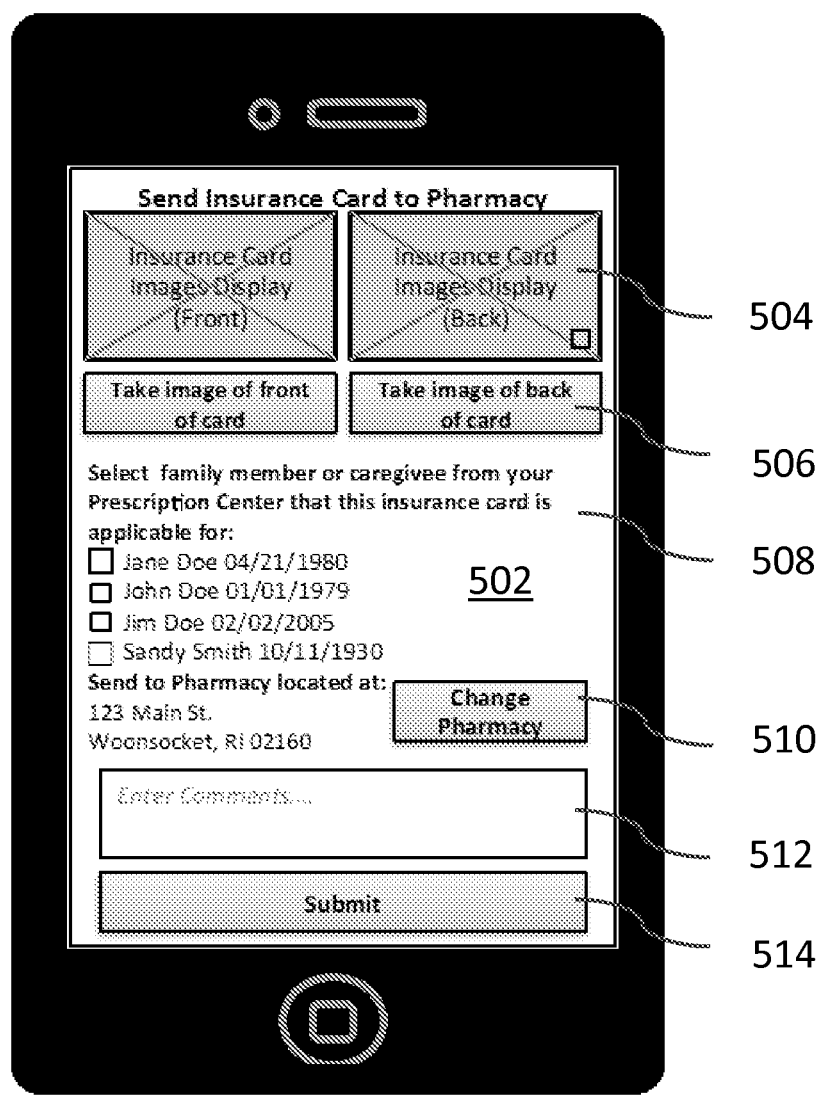
FIGS. 5 and 6 illustrate exemplary user interfaces in accordance with embodiments of the present invention.

FIG. 5 illustrates a device 500 that displays a graphical-user interface 502 in accordance with embodiments of the present invention in which a user of the device 500 is authenticated with a pharmacy service (e.g., the server 102). The interface 502 includes windows 504 for displaying previews and/or captured images and buttons 506 for initiating capture of the images. The interface 502 further includes an element 508 for displaying a list of family members and other people on behalf of whom the user may submit insurance information. Another element 510 displays a preferred, last-used, or most-frequently-used pharmacy and an input button that allows the user to change the selected pharmacy. The user may enter comments via an input element 512 via touch, keyboard, voice, or other means. A submit button 514 allows the user to submit the images and/or other information.

Figure 6:
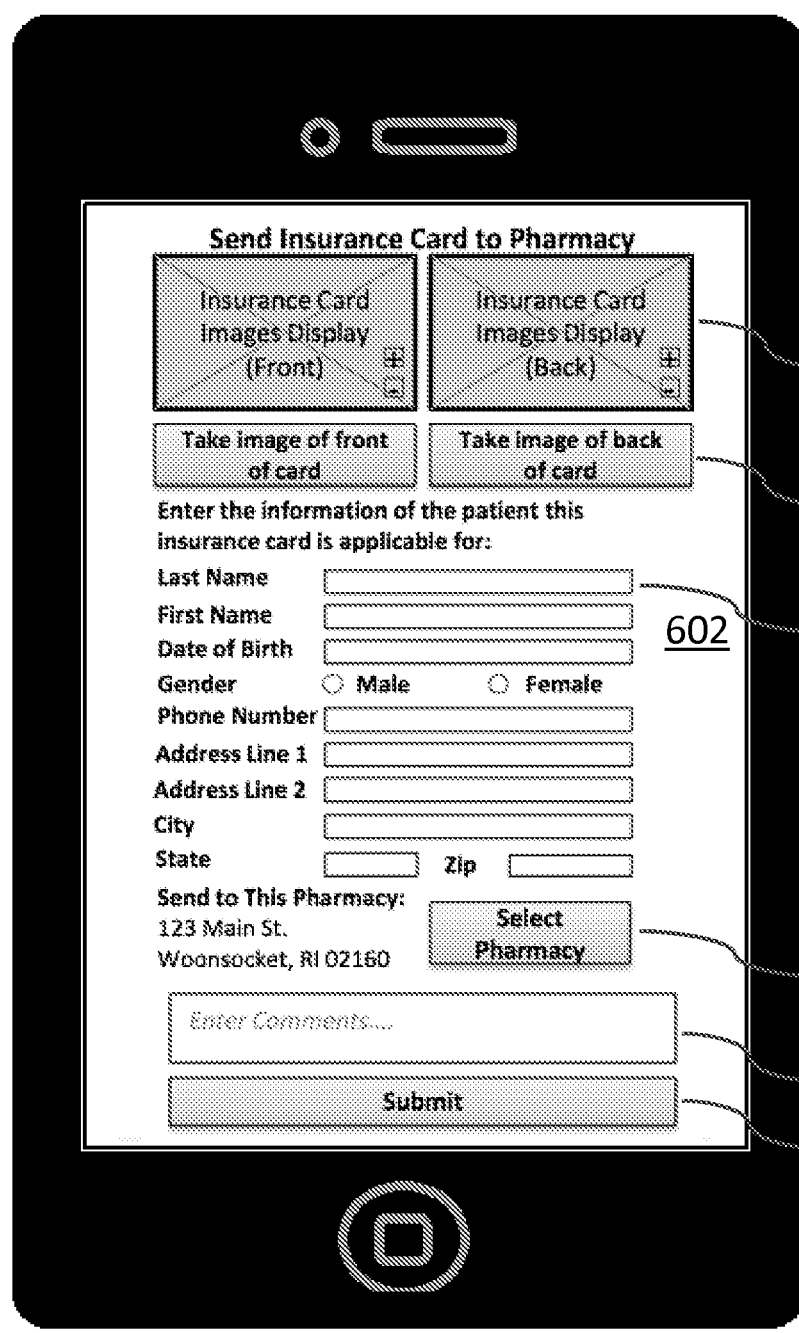

FIG. 6 illustrates a device 600 that displays a graphical-user interface 602 in accordance with embodiments of the present invention in which a user of the device 600 is not authenticated with a pharmacy service. As in FIG. 5, the interface 602 includes windows 604 for displaying previews and/or captured images and buttons 606 for initiating capture of the images. The interface 602 further includes, however, a plurality of input elements 608 for capturing patient information of the user or other person; the information may include last name, first name, date of birth, gender, phone number, address, city, state, and/or zip code. The interface 602 may also include a pharmacy selector 510, a comments field 612, and a submit button 614.

Figure 7:
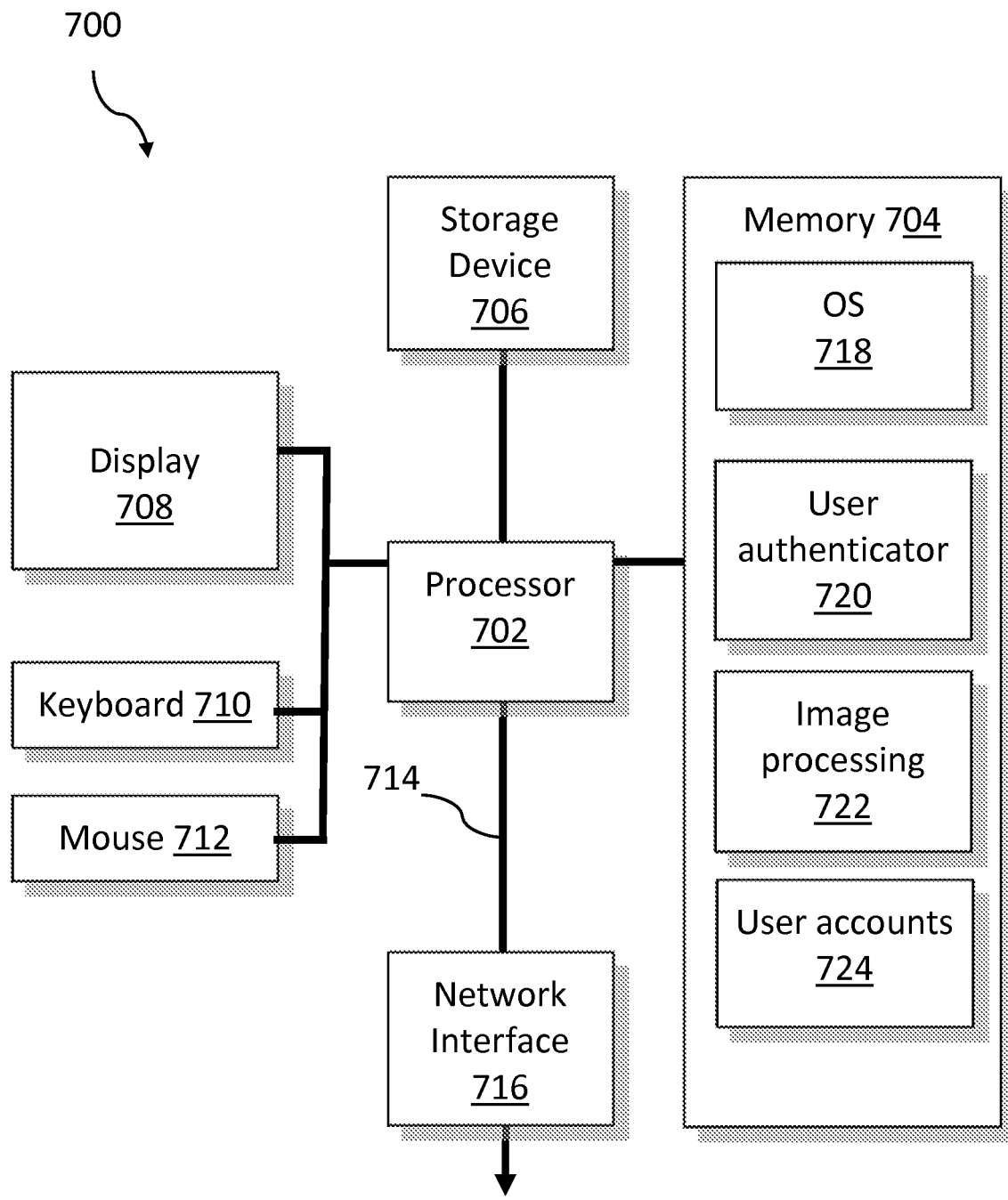
FIG. 7 illustrates a server system for updating insurance information in accordance with an embodiment of the present invention.

FIG. 7 is a simplified block diagram of a suitably programmed general-purpose server 700 implementing embodiments of the present invention. The server 700 includes a processor 702 having one or more central processing units (CPUs), volatile and/or non-volatile main memory 704 (e.g., RAM, ROM, or flash memory), one or more mass storage devices 706 (e.g., hard disks, or removable media such as CDs, DVDs, USB flash drives, etc. and associated media drivers), a display device 708 (e.g., a liquid-crystal display (LCD) monitor), user-input devices such as a keyboard 710 and a mouse 712, and one or more buses 714 (e.g., a single system bus shared between all components, or separate memory and peripheral buses) that facilitate communication between these components. A network interface 716 (e.g., a Wi-Fi or ETHERNET port) may be used to connect the computer 700 to the Internet or other network.

The main memory 704 may be used to store instructions to be executed by the processor 702, conceptually illustrated as a group of modules. These modules generally include an operating system 418 (e.g., a Microsoft WINDOWS, Linux, or APPLE OS X operating system) that directs the execution of low-level, basic system functions (such as memory allocation, file management, and the operation of mass storage devices), as well as higher-level software applications, such as a user authenticator 720 and an image-processing module 722. The various modules may be programmed in any suitable programming language, including, without limitation high-level languages such as C, C++, Java, Perl, Python, or Ruby or low-level assembly languages. The memory 704 may further store input and/or output data associated with execution of the instructions (including, e.g., user-account data 724) as well as additional information used by the various software applications.

Figure 8:
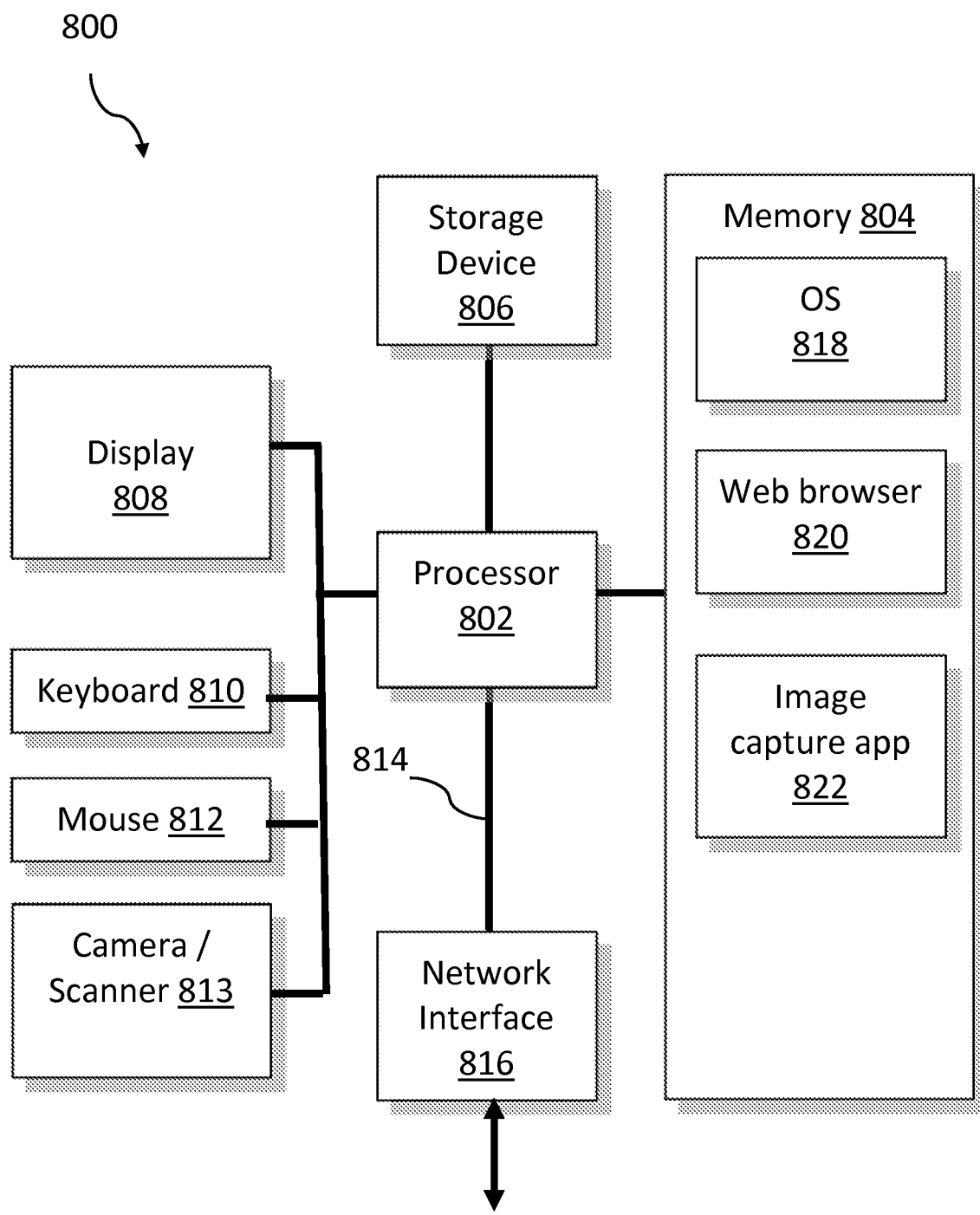
FIG. 8 illustrates a client system for updating insurance information in accordance with an embodiment of the present invention.

FIG. 8 is a simplified block diagram of a suitably programmed client device 800 for capturing information from a user and displaying an order status thereto. Like the server 700, the client device 800 includes a processor 802, a memory 804, a storage device 806, a display 808, a keyboard 810, a mouse 812, buses 814, and a network interface 816. The client 800 may further include a camera/scanner 813 for capturing images. The client 800 and the server 700 may communicate via a network such as the Internet using the network interfaces 716, 816. The user input and output interfaces described herein may be presented to the user via a web browser 820 and/or a client-native application 822.

The server 700 and client 800 are described herein with reference to particular blocks, but this description is not intended to limit the invention to a particular physical arrangement of distinct component parts. The computers 700, 800 are illustrative examples; variations and modifications are possible. The computers 700, 800 may be implemented in a variety of form factors, including server systems, desktop systems, laptop systems, tablets, smartphones or personal digital assistants, and so on. A particular implementation may include other functionality not described herein, e.g., wired and/or wireless network interfaces, media playing and/or recording capability, etc. In some embodiments, one or more cameras may be built into the computer rather than being supplied as separate components. Further, the computer processor may be a general-purpose microprocessor, but depending on implementation can alternatively be, e.g., a microcontroller, peripheral integrated circuit element, a customer-specific integrated circuit ("CSIC"), an application-specific integrated circuit ("ASIC"), a logic circuit, a digital signal processor ("DSP"), a programmable logic device such as a field-programmable gate array ("FPGA"), a programmable logic device ("PLD"), a programmable logic array ("PLA"), smart chip, or other device or arrangement of devices.

It should also be noted that embodiments of the present invention may be provided as one or more computer-readable programs embodied on or in one or more articles of manufacture. The article of manufacture may be any suitable hardware apparatus, such as, for example, a floppy disk, a hard disk, a CD ROM, a CD-RW, a CD-R, a DVD ROM, a DVD-RW, a DVD-R, a flash memory card, a PROM, a RAM, a ROM, or a magnetic tape. In general, the computer-readable programs may be implemented in any programming language. Some examples of languages that may be used include C, C++, or JAVA. The software programs may be further translated into machine language or virtual machine instructions and stored in a program file in that form. The program file may then be stored on or in one or more of the articles of manufacture.

Certain embodiments of the present invention were described above. It is, however, expressly noted that the present invention is not limited to those embodiments, but rather the intention is that additions and modifications to what was expressly described herein are also included within the scope of the invention. Moreover, it is to be understood that the features of the various embodiments described herein were not mutually exclusive and can exist in various combinations and permutations, even if such combinations or permutations were not made express herein, without departing from the spirit and scope of the invention. In fact, variations, modifications, and other implementations of what was described herein will occur to those of ordinary skill in the art without departing from the spirit and the scope of the invention. As such, the invention is not to be defined only by the preceding illustrative description.

What is claimed is:

1. A system comprising:
   a computer memory for storing extracted information from a card;
   a network interface configured for receiving extracted information from a client device of a user over a computer network; and
   a computer processor configured for executing software instructions to, responsive to arrival of a detection event associated with the card being new or expired, cause an application to automatically launch on the client device, wherein the application launched on the client device is configured to:
      detect whether the user is authenticated with a pharmacy service, wherein the pharmacy service comprises patient information;
      if the user is authenticated with the pharmacy service, cause a first graphical-user interface to be displayed to the user on a screen of the client device, wherein the first graphical-user interface comprises a prompt to capture the extracted information from the card;
      if the user is not authenticated with the pharmacy service, cause a second graphical-user interface to be displayed to the user on the screen of the client device, wherein the second graphical-user interface comprises:
         the prompt to capture the extracted information from card; and
         a data-entry prompt for capturing patient information;
      capture extracted information from the card; and
      electronically transmit the patient information and the extracted information from the card to a pharmacy for processing.

2. The system of claim 1, wherein the application is further configured to:
   capture an image of the card; and
   extract the extracted information from the image of the card.

3. The system of claim 2, wherein extracting the extracted information from the image of the card comprises optical-character recognition, cropping, or scanning a barcode.

4. The system of claim 2, wherein:
   the client device includes the computer memory and an image capture device; and
   capturing the image of the card includes storing the image in the computer memory from the image capture device.

5. The system of claim 1, wherein the card is an insurance card associated with the user.

6. The system of claim 1, wherein the detection event comprises the pharmacy service sending a notification of a new or expired card to the client device.

7. The system of claim 6, wherein the detection event further comprises the pharmacy service detecting the new or expired card in response to:
   the user using the new or expired card; or
   arrival of a known expiration date.

8. The system of claim 1, wherein the detection event comprises the user detecting a new or expired card and indicating on the client device that an update to the card is needed.

9. A method comprising:
   responsive to arrival of a detection event associated with a card being new or expired, causing an application to automatically launch on a client device of a user, wherein the application launched on the client devices is configured to:
      detect whether the user of the client device is authenticated with a pharmacy service, wherein the pharmacy service comprises patient information;
      if the user is authenticated with the pharmacy service, cause a first graphical-user interface to be displayed to the user on a screen of the client device, wherein the first graphical-user interface comprises a prompt to capture an image of an insurance card;
      if the user is not authenticated with the pharmacy service, cause a second graphical-user interface to be displayed to the user on the screen of the client device, wherein the second graphical-user interface comprises:
         the prompt to capture the image of the insurance card; and
         a data-entry prompt for capturing patient information;

capture extracted information from the card; and electronically transmit the patient information and the extracted information from the card to a pharmacy for processing.

10. The method of claim 9, wherein the application is further configured to:

capture an image of the card; and extract the extracted information from the image of the card.

11. The method of claim 10, wherein extracting the extracted information from the image of the card comprises optical-character recognition, cropping, or scanning a barcode.

12. The method of claim 10, wherein:

the client device includes a computer memory and an image capture device; and capturing the image of the card includes storing the image in the computer memory from the image capture device.

13. The method of claim 9, wherein the card is an insurance card associated with the user.

14. The method of claim 9, wherein the detection event comprises the pharmacy service sending a notification of a new or expired card to the client device.

15. The method of claim 14, wherein the detection event further comprises the pharmacy service detecting the new or expired card in response to:

the user using the new or expired card; or arrival of a known expiration date.

16. The method of claim 9, wherein the detection event comprises the user detecting a new or expired card and indicating on the client device that an update to the insurance card is needed.

17. A system comprising:

a computer memory for storing extracted information from an image of a new or updated card;

a network interface configured for receiving extracted information from a client device of a user over a computer network; and a computer processor configured for executing software instructions to, responsive to arrival of a detection event associated with the new or updated card, cause an application to automatically launch on the client device, wherein the application launched on the client device is configured to:

detect whether the user is authenticated with a pharmacy service, wherein the pharmacy service comprises patient information;

if the user is authenticated with the pharmacy service, cause a first graphical-user interface to be displayed to the user on a screen of the client device, wherein the first graphical-user interface comprises a prompt to capture the image;

if the user is not authenticated with the pharmacy service, cause a second graphical-user interface to be displayed to the user on the screen of the client device, wherein the second graphical-user interface comprises:

the prompt to capture the image of the new or updated card; and a data-entry prompt for capturing patient information;

capture extracted information from the image of the new or updated card; and electronically transmit the patient information and the extracted information from the image to a pharmacy for processing.

18. The system of claim 17, wherein the application is further configured to:

capture the image of the new or updated card using an image capture device of the client device; and extract the extracted information from the image of the new or updated card.

19. The system of claim 17, wherein the detection event comprises the pharmacy service sending a notification of a new or expired card to the client device.

20. The system of claim 17, wherein the detection event comprises the user detecting a new or expired card and indicating on the client device that an update to the card is needed.

* * * * *